(12) United States Patent
Farber (10) Patent No.: US 10,180,408 B1
(45) Date of Patent: Jan. 15, 2019

(54) METHOD OF SENSOR CONDITIONING FOR IMPROVING SIGNAL OUTPUT STABILITY FOR MIXED GAS MEASUREMENTS

(71) Applicant: Boris Farber, Solon, OH (US)

(72) Inventor: Boris Farber, Solon, OH (US)

(73) Assignee: BJR SENSORS LLC, Solon, OH (US)

( * ) Notice: Subject to any disclaimer, the term of this patent is extended or adjusted under 35 U.S.C. 154(b) by 129 days.

(21) Appl. No.: 15/090,792

(22) Filed: Apr. 5, 2016

(51) Int. Cl.
*G01N 27/406* (2006.01)
*G01N 27/417* (2006.01)
*G01N 27/407* (2006.01)
*G01N 27/416* (2006.01)

(52) U.S. Cl.
CPC ..... *G01N 27/4067* (2013.01); *G01N 27/4062* (2013.01); *G01N 27/4071* (2013.01); *G01N 27/417* (2013.01); *G01N 27/4165* (2013.01)

(58) Field of Classification Search
CPC ... G01N 27/4065; G01N 27/409; G01N 27/41
See application file for complete search history.

(56) References Cited

U.S. PATENT DOCUMENTS

| | | | |
|---|---|---|---|
| 6,800,158 B2 | 10/2004 | Polikarpus et al. | |
| 2005/0284772 A1* | 12/2005 | Farber | G01N 27/4065 205/775 |

* cited by examiner

*Primary Examiner* — Alexander S Noguerola
(74) *Attorney, Agent, or Firm* — John D. Gugliotta (57) ABSTRACT

A method of treating a gas sensor with an improved pulse discharge technique is provided by adding measurements of additional parameters, modification of the data processing algorithm, and establishing new calibration procedure in the low, intermediate and high concentration ranges of $NO_x$. Additional measurements of the charge transfer during the charging pulses of the pulse discharge technique are made, and utilizing these data in combination with discharge rates during the pauses of the pulse discharge technique allows for combined measurements of $O_2$ and $NO_x$, in the combustion exhaust.

17 Claims, 13 Drawing Sheets

FIG. 1

PRIOR ART

PRIOR ART
FIG. 2

PRIOR ART

FIG. 3

PRIOR ART

METHOD OF SENSOR CONDITIONING FOR IMPROVING SIGNAL OUTPUT STABILITY FOR MIXED GAS MEASUREMENTS

RELATED APPLICATIONS

This invention incorporates by reference all the subject matter of the related applications as if it is fully rewritten herein.

BACKGROUND OF THE INVENTION

1. Field of the Invention

The present invention relates generally to an improvement in the present inventor's method or technique, as claimed in the related art, of conditioning a gas sensor through the application of pulse discharges in order to condition mixed-potential gas sensors for detecting gases commonly found in combustion exhaust throughout a wider temperature range.

2. Description of the Related Art

Figure 1:
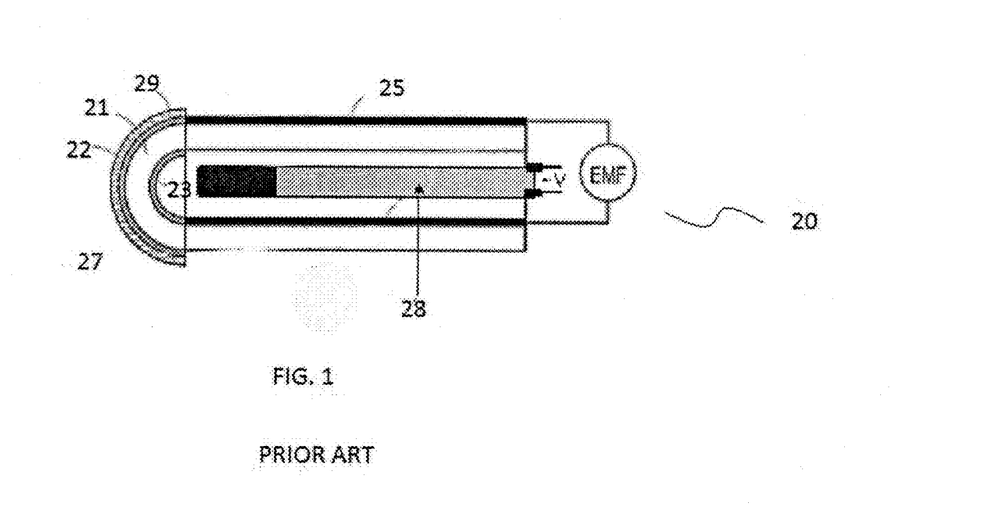
FIG. 1 is a schematic of zirconia oxygen thimble sensor according to the PRIOR ART.
Figure 2:
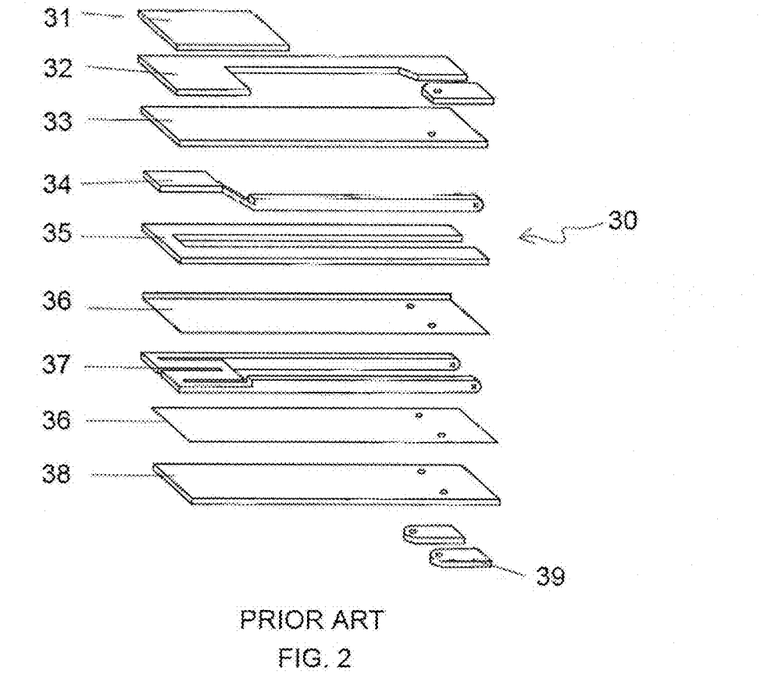
FIG. 2 is a schematic of a commercial zirconia oxygen planar sensor according to the PRIOR ART.

The sensing element used in zirconia oxygen sensors is generally formed of an impermeable zirconia layer separating two porous electrodes, which are typically made of platinum metal. The electrodes are then used to measure the differential oxygen concentration between the measured gas on the outside of the sensor, and a reference gas, usually atmospheric, on the inside of the sensor. By measuring the voltage between two electrodes, the differential oxygen concentration can be calculated. Sensor design has a form of either thimble cell is shown according to the PRIOR ART in FIG. 1. Such a sensor 20 includes a zirconia substrate 21, a measuring electrode 22, a reference electrode 23, connecting leads 24, 25, and a pencil heater 28. The sensor design may further be in stacked planar layers as shown in FIG. 2 according to the PRIOR ART. Such a sensor 30 includes a porous protective layer 31, an external electrode 32, a sensor laminate 33, an internal electrode 34, reference air laminate 35, an insulation layer 36, a heater 37 and a heater laminate 38, with electrical current provided through connection contacts 39. In both cases sensor design include an internal heater to maintain sensor temperature in the desired temperature range.

Figure 3:
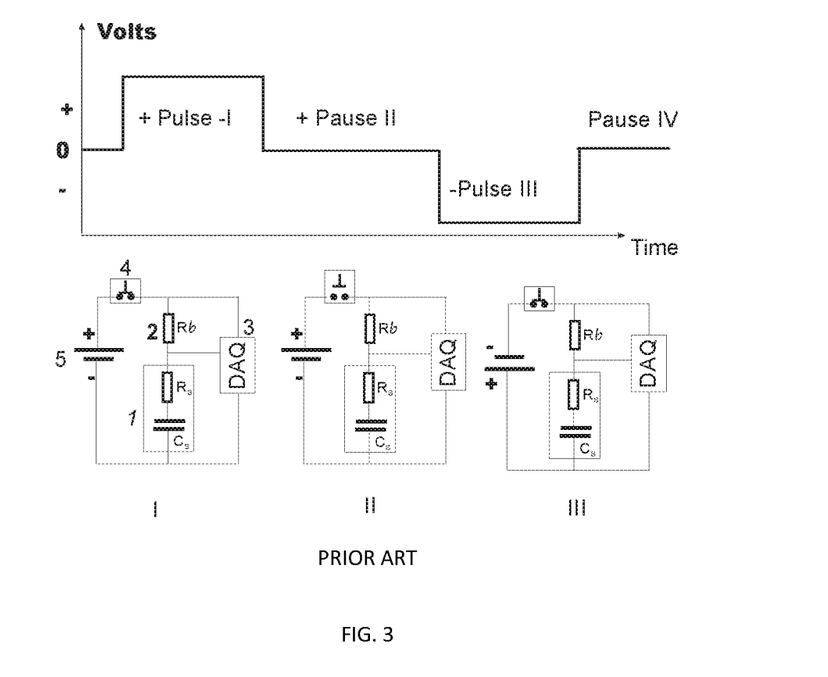
FIG. 3 is a schematic representation of the sensor conditioning in accordance with the PRIOR ART.
Figure 4:
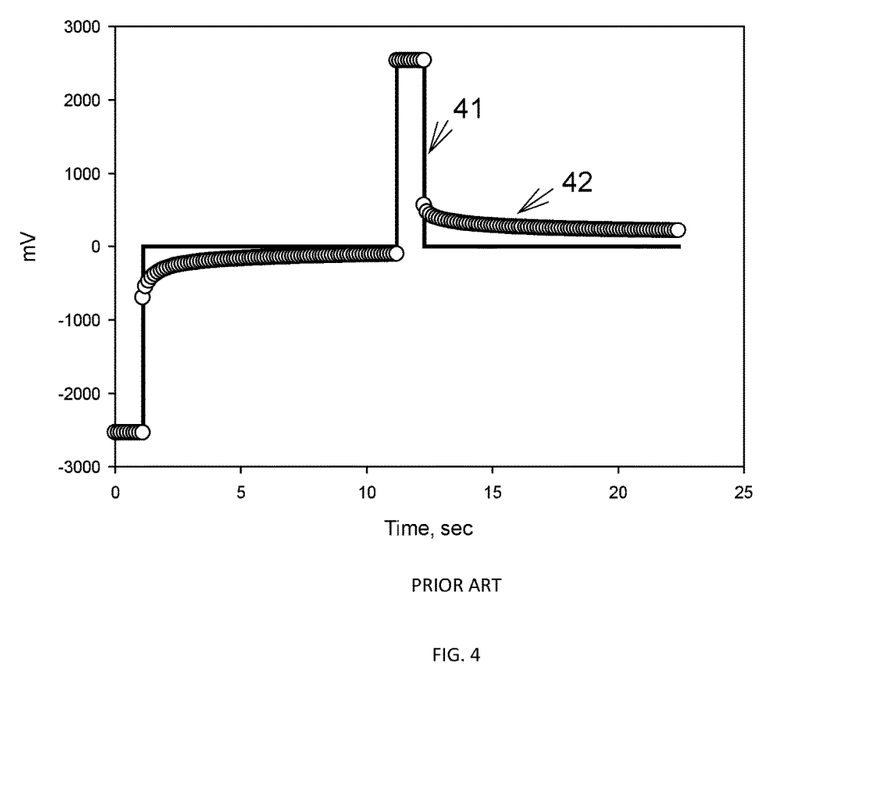
FIG. 4 is a chart indicating applied (1) and measured (2) voltage between sensor electrodes during the Pulse Discharge Technique in accordance with the PRIOR ART.

An improved method for activating such sensors is described in the inventor's own related prior art reflected in U.S. Pat. No. 7,585,402 and recently awarded U.S. Pat. No 9,304,101. A typical schematic of the pulse discharge technique according to this PRIOR ART is shown in FIG. 3 and described below, which is a representation of the sensor conditioning in accordance with the previous invention. During the charging phases of the Pulse Discharge Technique or PDT (I and III) sensor was connected to the charging power source, during the discharging phases (II and IV) sensor was disconnected from the charging power source and kinetics of the sensor discharge was measured. FIG. 4 further shows applied voltage 41 and measured voltage 42 between the sensor electrodes in accordance with a prior art.

Figure 5:
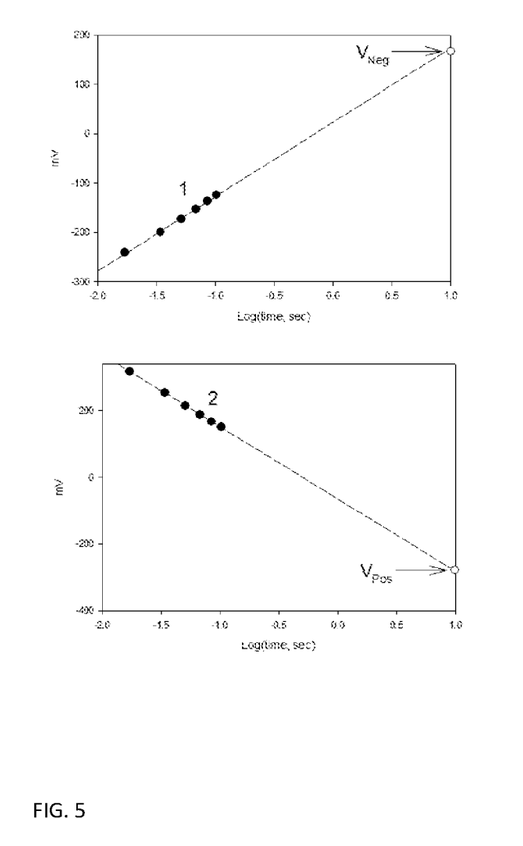
FIG. 5 is a graph depicting measurements of the sensor output during the Pulse Discharge Technique in accordance with the PRIOR ART, wherein curve 1 depicts sensor output following negative charging voltage applied between the sensor electrodes and curve 2 depicts sensor output following positive charging voltage applied between the sensor electrodes.

Sensor response to varying concentrations of the analyzed gas was measured by:
  a. linearization of the sensor discharge data recorded during the pauses between charging pulses in mv versus Log(t) coordinates; and
  b. extrapolation of the linear regression line to the fixed pause time of 10 sec as shown in FIG. 5.

This approach provided for accurate and low level detection of the $NO_x$ concentrations in the combustion exhaust. However, several limitations related to a limited $NO_x$ concentration measurement range and strong cross-interference from Oxygen concentration variations (for sensor operating temperature T>400° C.), were revealed, which are described based on the following examples.

EXAMPLE 1

Nitrogen Oxide (NO) Measurements With an Automotive Thimble-Type Lambda Sensor at the Sensor Operating Temperature=350° C.

Figure 6:
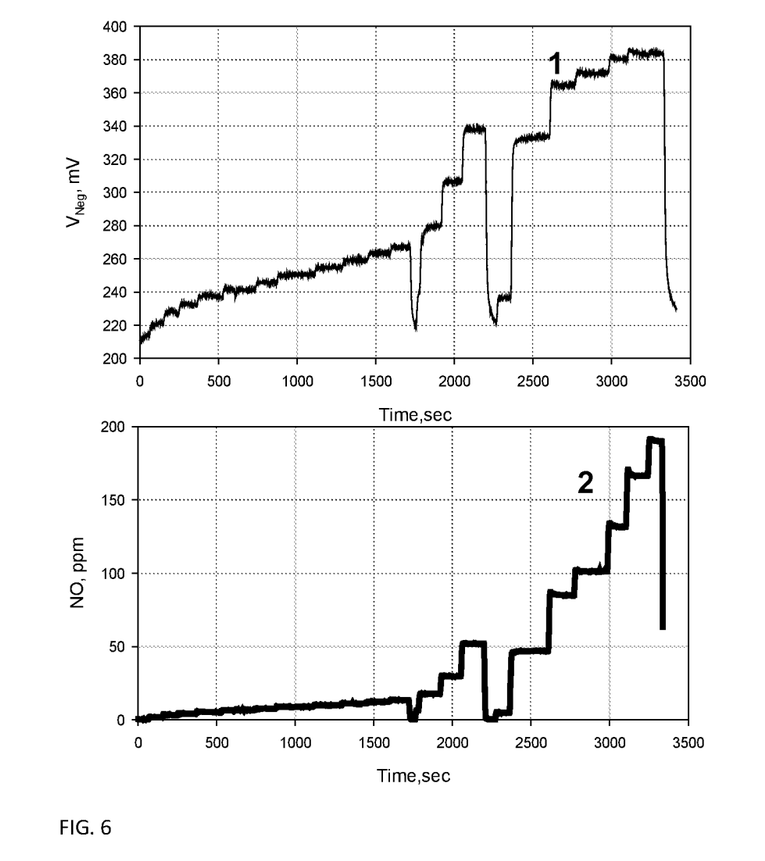
FIG. 6 is a graph depicting sensor output as $V_{Neg}$ values (1) in response to varying concentration of NO shown in 2 (as measured with a bench-top extractive analyzer) under test conditions comprising: Sensor Temperature=350° C.; $O_2$ ~10%, $H_2O$ ~7%, $CO_2$ ~8%, Ethene ~100 ppm, balance $N_2$; Gas flow rate=20 l/min. Pulse duration=102 ms, Pause duration=119 ms. Amplitude=2.5 V, with data processing performed in accordance with the PRIOR ART.

FIG. 6 curve 1 shows sensor output values ($V_{Neg}$) determined in accordance with the PRIOR ART approach in response to varying concentrations of NO shown in curve 2 (measured with an extractive bench-top NO analyzer). Sensor output is highly sensitive and can reliably detect low level NO values (<10 ppm). However, at higher concentrations of NO (>100 ppm), sensor output signal was saturating and was no longer increasing in response to rising concentrations of NO.

EXAMPLE 2

Nitrogen Oxide (NO) Measurements With an Automotive Planar-Type Lambda Sensor at the Sensor Operating Temperature=480° C.

Figure 7:
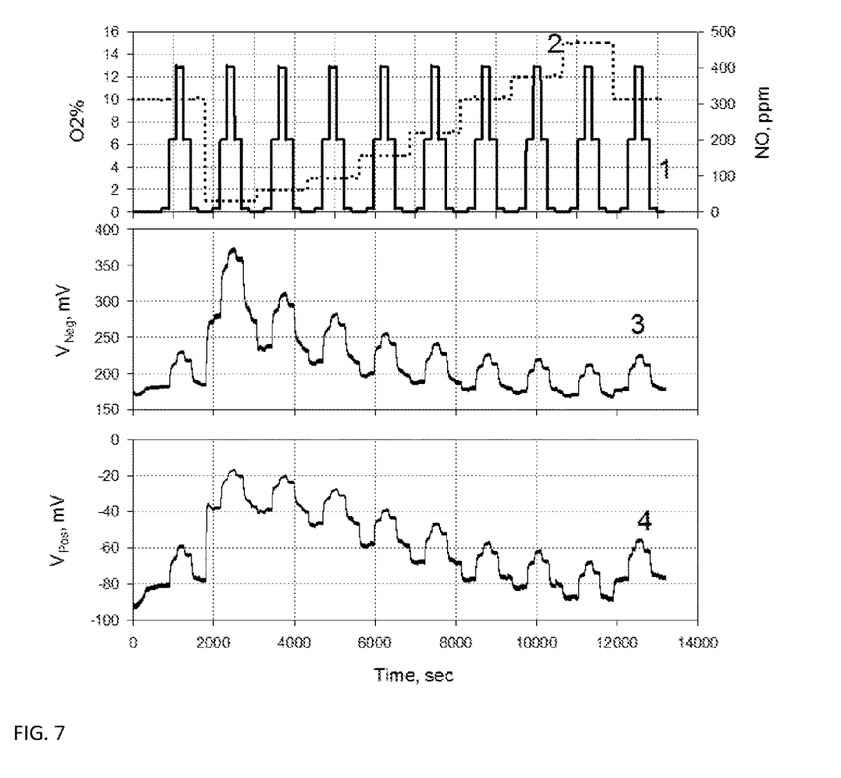
FIG. 7 is a graph depicting sensor output as $V_{Neg}$ (3) and $V_{Pos}$ (4) values in response to varying concentration of NO (1) and $O_2$ (2), under test conditions comprising: Sensor Temperature=480° C.; $O_2$ ~1-15%, $H_2O$ ~10%, $CO_2$ ~10%, balance $N_2$; Gas flow rate=2 l/min, with data processing performed in accordance with the PRIOR ART.

At higher sensor operating temperatures changes in the oxygen concentration in the analyzed gas were interfering with the sensor response to changing concentrations of NO as shown in FIG. 7 for both $V_{Neg}$ and $V_{Pos}$ sensor responses. Oxygen concentration was varied from 1 to 15 $O_2$% (curve 2) and NO concentration was varied from 0 to 400 ppm (curve 1). Increase in $O_2$ concentration decreased sensor output for both $V_{Neg}$ and $V_{Pos}$, while increase in the NO concentration—increased sensor output.

As demonstrated, under these circumstances, measured data are not sufficient for independent measurements of $O_2$ and NO.

SUMMARY OF THE INVENTION

An improvement to the pulse discharge technique is suggested by adding measurements of additional parameters, modification of the data processing algorithm, and establishing new calibration procedure in the low, intermediate and high concentration ranges of $NO_x$.

Additional improvement is suggested by including measurements of the charge transfer during the charging pulses of the pulse discharge technique and utilizing these data in combination with discharge rates during the pauses of the pulse discharge technique for combined measurements of $O_2$ and $NO_x$ in the combustion exhaust.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 8-14.

Figure 8:
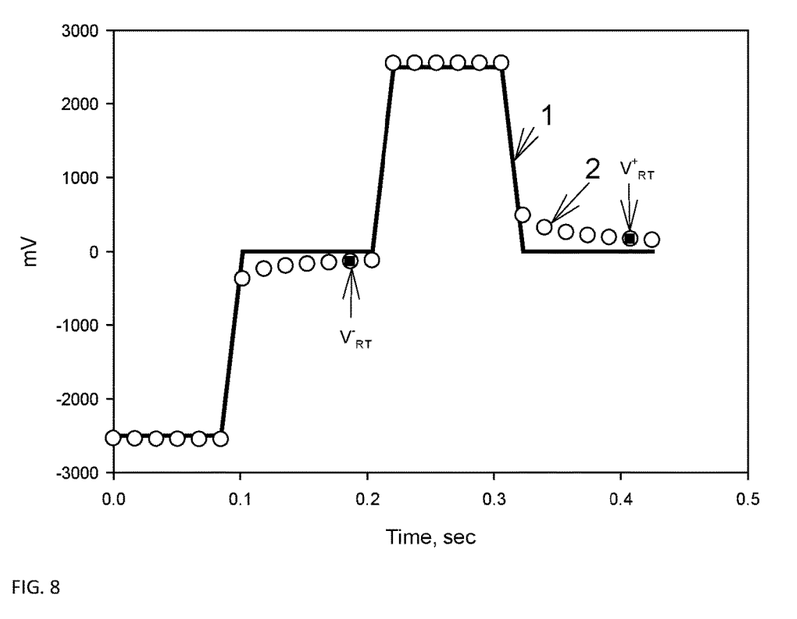
FIG. 8 depicts an alternative sensor output determination as the voltage measured between the sensor electrodes at a fixed elapsed time during the pauses between the charging pulses. 1-applied voltage, 2-measured voltage, $V^{-RT}$-sensor output (at a read time) following Negative charging pulse. $V^{+RT}$ sensor output (at a read time) following Positive charging pulse.

To address the sensor response saturation at high concentrations of NO in the combustion exhaust, an improved method of the sensor response measurements is provided as generally shown in FIG. 8. Sensor response is measured as a differential voltage between two sensor electrodes at a fixed elapsed time during the pauses following charging pulses of negative and positive polarity. Sensor outputs are depicted as $V^{-RT}$ and $V^{+RT}$ following the negative and positive pulses.

Figure 9:
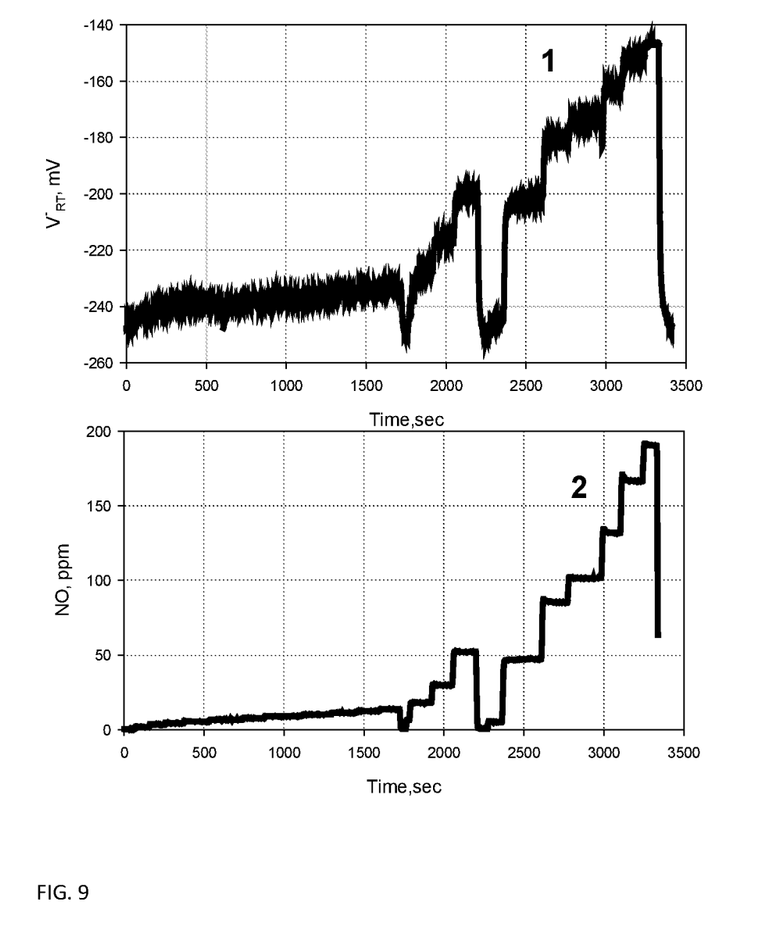
FIG. 9 is a graph depicting sensor output as $V^{-RT}$ values (1) in response to varying concentration of NO shown in 2 (as measured with a bench-top extractive analyzer), under test conditions comprising: Sensor Temperature=350° C.; $O_2$ ~10%, $H_2O$ ~7%, $CO_2$ ~8%, Ethene ~100 ppm, balance $N_2$; Gas flow rate=20 l/min.

FIG. 9 shows $V^{-RT}$ values (1) measured at the same conditions as shown in FIG. 6. There is no saturation in the as determined sensor response to increasing values of NO at concentrations >100 ppm. The combination of $V_{Neg}$ and $V^{-RT}$ values at low (<100 ppm) and high (>100 ppm) respectively are herein used to establish calibration curves to maintain high measurement accuracy at low and high concentrations of the $NO_x$ in the analyzed combustion exhaust.

Figure 10:
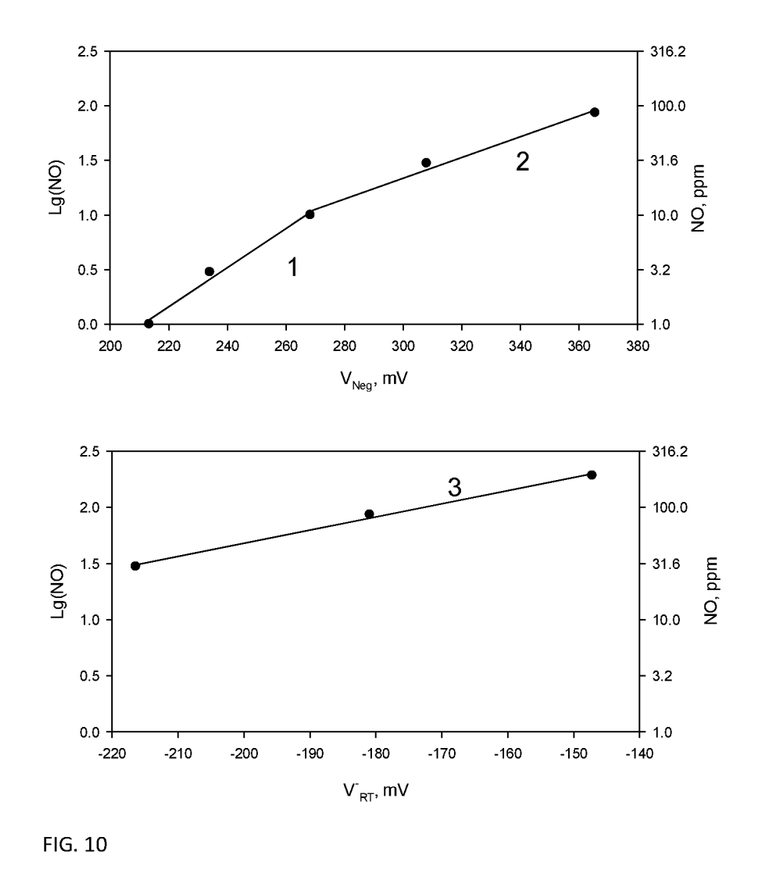
FIG. 10 depicts calibration curves for the sensor output in the low (<10 ppm) and intermediate (10-100 ppm) NO concentration ranges as $V_{Neg}$ versus Log (NO) in 1 and 2. Calibration for high NO range (>100 ppm) as $V^{-RY}$ versus Log (NO) (3)

FIG. 10 shows a suggested calibration procedure in accordance with a preferred embodiment. The sensor response is determined as $V_{Neg}$ for NO concentration<100 ppm. Three calibration ranges are suggested:

1. NO<10 ppm (1); Sensor response is determined as $v_{neg}$;
2. 10 ppm<NO<100 ppm (2); Sensor response is determined as $v_{neg}$; and
3. 100 ppm<NO (3); Sensor response is determined as $V^{-RT}$.

Figure 11:
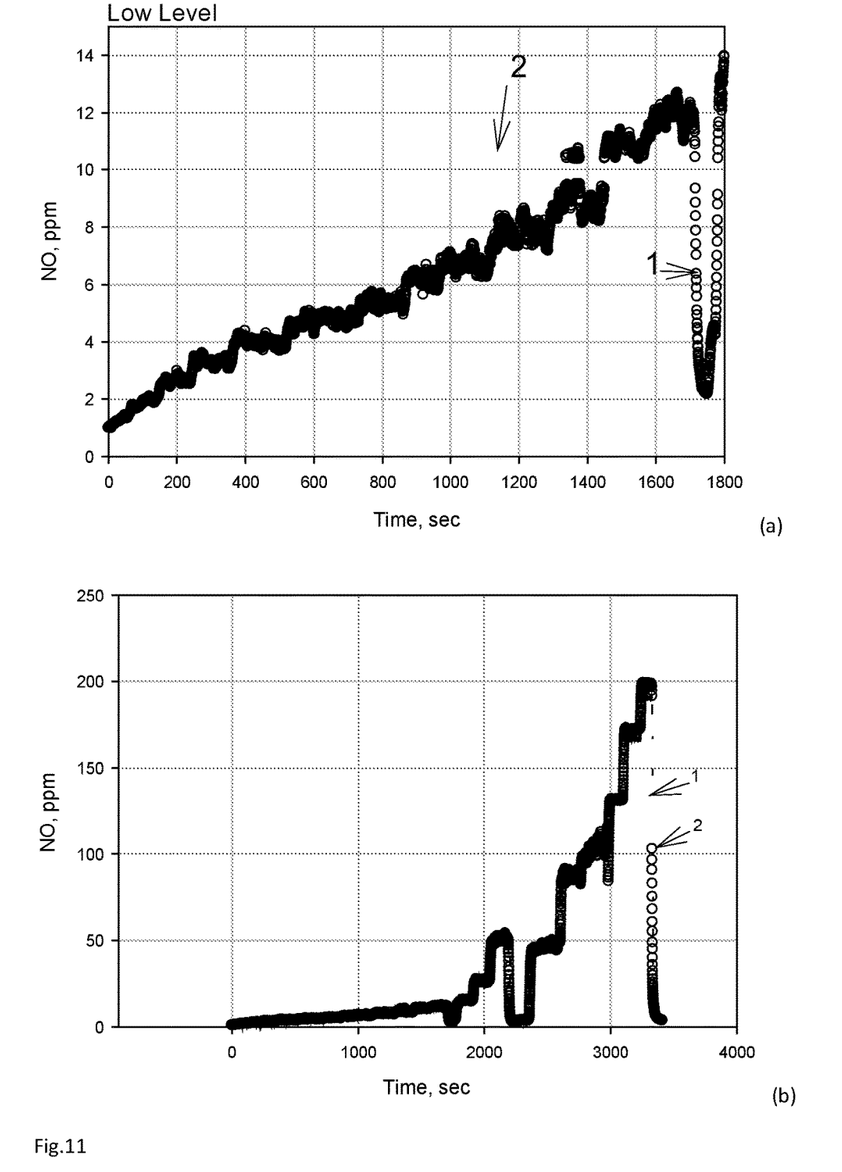
FIG. 11 is a graph showing comparison between data measured with the Pulse Discharge Technique NO concentrations and applied NO values, wherein low ppm range is shown in (a) and the full range is shown in (b) and wherein 1 is measured values (closed circles), 2 is applied values (dotted line), with data collected under the conditions are shown in FIG. 9 and FIG. 10.

By using this suggested calibration procedure, high accuracy measurements were performed as demonstrated in FIG. 11. Measured with the Pulse Discharge Technique values of NO were closely matching values measured with a high precision extractive bench top analyzer at low (<10 ppm) (FIG. 11a), intermediate (10<NO<100 ppm) and high (NO>100 ppm) ranges (FIG. 11b).

Further intended by the current invention are additional improvements suggested to address strong interference between varying concentration of oxygen and $NO_x$ at relatively high sensor operating temperatures (T>400° C.).

In accordance with a PRIOR ART approach (U.S. Pat. No. 7,585,402 and U.S. Pat. No. 9,304,101) charging currents were measured during the charging pulses of the pulse discharge technique. In accordance with a preferred embodiment, it is an aspect of the present invention to measure charge transfer during the charging pulse by using integration of the measured current as shown in the following equation:

$$Q = \int_0^{tpulse} I(t) * dt \quad (1)$$

By using differential charge transfer values ($\Delta Q$) between positive and negative pulses of the Pulse Discharge Technique in combination of $V_{Neg}$ sensor response values we were able to simultaneously measure Oxygen and NO concentration. Data processing algorithm is shown in FIG. 12 and FIG. 13.

Figure 12:
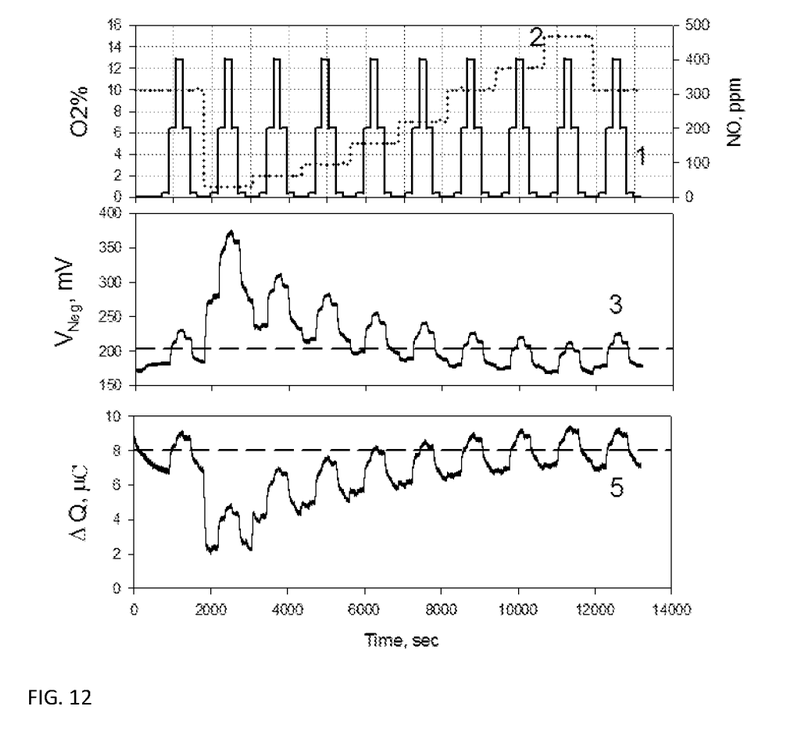
FIG. 12 is a graph depicting sensor output as $V_{Neg}$ (3) and the differential charge transfer during the Positive and Negative charging pulses (5) in response to varying concentration of NO (1) and $O_2$ (2), under test conditions as shown in FIG. 7.
Figure 13:
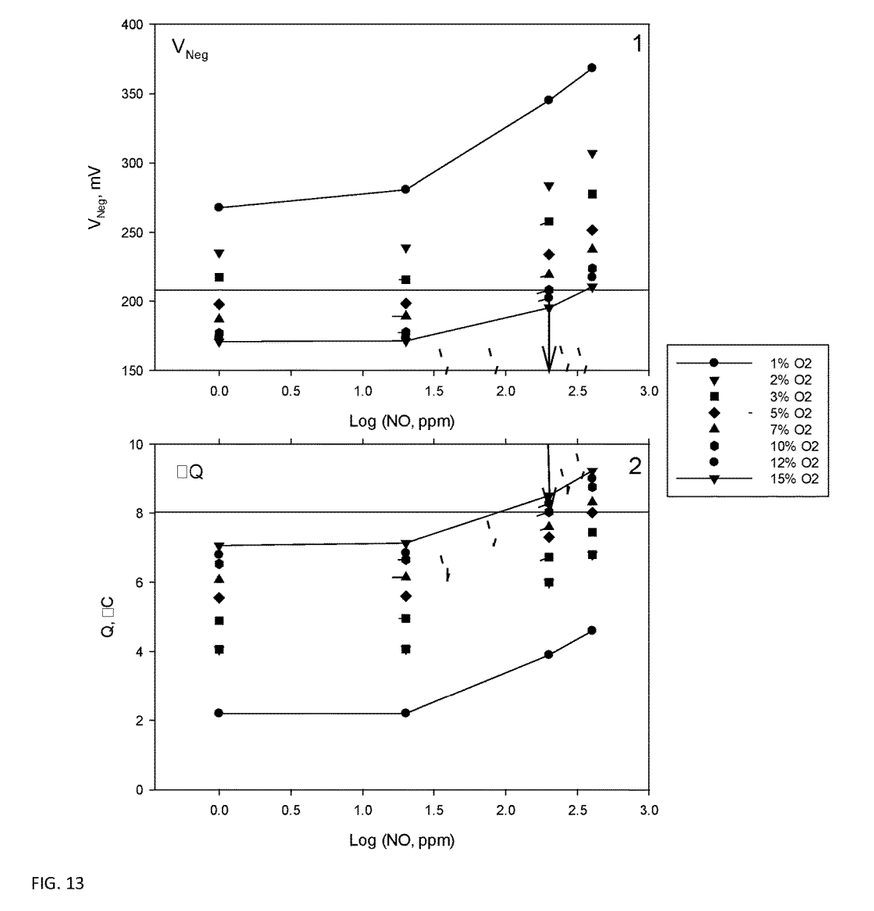
FIG. 13 depicts a data processing algorithm for combined measurements of NO and $O_2$.

Referring in conjunction with FIG. 12 is show that increase in the NO concentration lead to increase in the $V_{Neg}$ sensor response and increase in the $\Delta Q$. On the other hand, increase in the oxygen concentration lead to decrease of $V_{Neg}$ and increase in the $\Delta Q$. To determine concentration values of (NO, ppm and O2 %) corresponding to a measured pair of $V_{Neg}$ and $\Delta Q$ (for example $V_{Neg}$=204 mV and $\Delta Q$=8.0 µC), the following data processing algorithm was used.

FIG. 12 further shows that a line corresponding to a constant values of $V_{Neg}$ and $\Delta Q$ intersect measurement curves at multiple data points, which indicate that a fixed value of $V_{Neg}$ or $\Delta Q$ can correspond to multiple combinations of ($O_2$%, NO, ppm). To define a unique combination of ($O_2$%, NO, ppm) corresponding to a pair of measured parameters ($V_{Neg}$=204 mV ;$\Delta Q$=8.0 µC), the data is re-plotted in coordinates of $V_{Neg}$ versus Log(NO) and $\Delta Q$ versus Log(NO) as shown in conjunction with FIG. 13. Lines of constant measured parameters of $V_{Neg}$ and $\Delta Q$ intersect calibration curves in multiple points. These possible intercession values are shown in Tables 1 and 2. For a fixed value of $V_{Neg}$ there are multiple combinations of $O_2$%, NO and $\Delta Q$ are possible. For a fixed value of $\Delta Q$ there are multiple combinations of $O_2$%, NO and $V_{Neg}$ are possible. However, these two sets of data are converging in a single value of $O_2$% and NO, corresponding to a fixed combination of $V_{Neg}$=204 mV and $\Delta Q$=8.0 µC, leading to determination of $O_2$=10% and NO=204 ppm.

Figure 14:
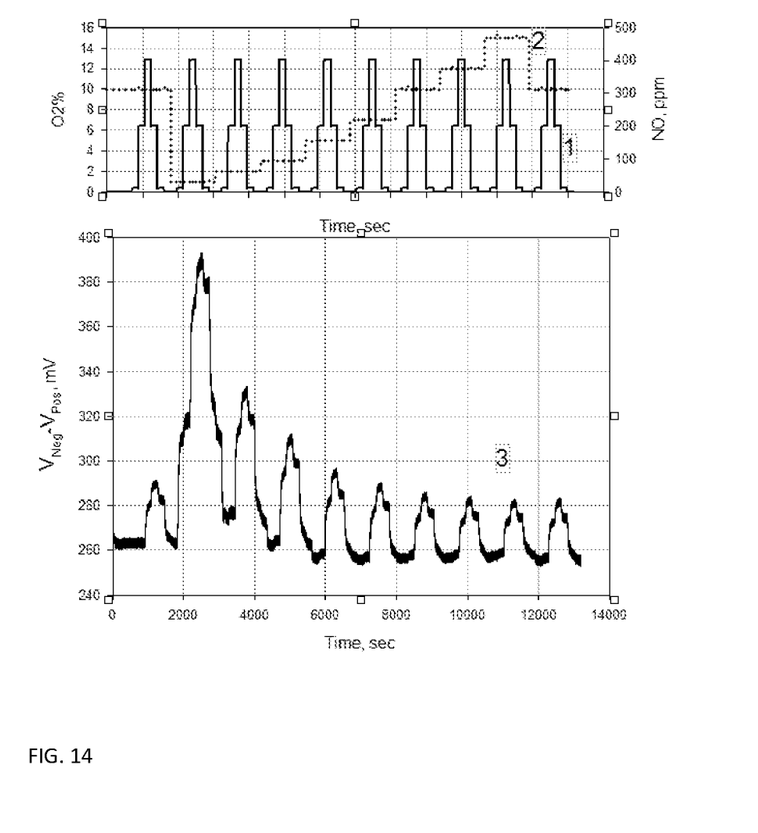
FIG. 14 Sensor output as ($V_{Neg}$- $V_{Pos}$) (3) under varying $O_2$% (2) and NO, ppm (1) under test conditions shown in FIG. 7.

Additionally, FIG. 14 shows that a simplified method of oxygen concentration cross-interference on the sensor output under varying $NO_x$ concentrations can be established by calculating $V_{Neg}$-$V_{Pos}$ values and using this difference as a sensor response parameter. In the $O_2$% concentration range between 5-15% sensor output is practically independent off the $O_2$% concentration.

TABLE 1

Possible combinations of $O_2$ % and NO, ppm leading to a constant value of $V_{Neg}$ = 204 mV.

| O2 % | Log(NO) | NO, ppm | $\Delta Q$, µC |
|---|---|---|---|
| 5 | 1.57 | 37 | 6.1 |
| 7 | 1.92 | 83 | 7.1 |
| 10 | 2.31 | 204 | 8.0 |
| 12 | 2.42 | 263 | 8.5 |
| 15 | 2.55 | 355 | 9.1 |

TABLE 2

Possible combinations of $O_2$ % and NO, ppm leading to a constant value of $\Delta Q$ = 8.0, µC.

| O2 % | Log(NO) | NO, ppm | mV |
|---|---|---|---|
| 5 | 2.6 | 398 | 252 |
| 7 | 2.48 | 302 | 229 |
| 10 | 2.31 | 204 | 204 |
| 12 | 2.12 | 132 | 197 |
| 15 | 1.95 | 89 | 186 |

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. An improved pulse discharge technique comprising the steps:
    (a) applying a voltage pulse of positive polarity and fixed amplitude and duration between at least two sensor electrodes by connecting sensor electrodes with a charging power supply;
    (b) applying a pause for a fixed duration when the charging power supply is disconnected from the sensor electrodes, and recording the sensor discharge;
    (c) applying a next voltage pulse of negative polarity having the same fixed amplitude and same duration as the voltage pulse applied in step (a) by connecting said sensor electrodes with the charging power supply; and
    (d) applying a next pause with a fixed duration equal to the duration of the pause in step (b) when said charging power supply is disconnected from said sensor electrodes, and recording the sensor discharge during the next pause;
    (e) measuring sensor electrode output voltage during each of said pauses following each of said positive and said negative voltage pulses;
    (f) approximating sensor discharge voltage by means of equation V=S*Log(t) +C, wherein S is a slope and C is a constant calculated from a linear regression of an initial part of a discharge curve in semi-logarithmic coordinates where V∝Log(t), and t is a time elapsed during said pause;
    (g) determining extrapolated discharge sensor voltage values at a fixed time $t_0$ elapsed during each said pause following negative ($V_{Neg}$) and positive ($V_{Pos}$) voltage pulse by determining an extrapolated discharge sensor voltage value at a fixed elapsed time $t_0$; and
    (h) measuring the sensor electrode output as a voltage between the sensor electrodes at the fixed elapsed $t_0$ time during the pauses following the negative ($V_{Neg}$) and positive ($V_{Pos}$) voltage pulses.

2. The improved pulse discharge technique of claim 1, further comprising the step:
    (i) establishing calibration curves as a relation between measured ($V_{Neg}$) and analyzed gas concentration ($G_c$) in the form:

$$V_{Neg} \propto \text{Log}(G_c)$$

for low and intermediate analyzed gas concentrations, which are gas concentration in the range of 0-100 ppm.

3. The improved pulse discharge technique of claim 2, further comprising the step:
    (j) establishing calibration curves as a relation between measured ($V^{-RT}$) and analyzed gas concentration ($G_c$) in the form:

$$V^{-RT} \propto \text{Log}(G_c)$$

for high analyzed gas concentrations, which are gas concentration >100 ppm.

4. The improved pulse discharge technique of claim 3, further comprising the step:
    (l) measuring charge transfer during the negative ($V_{Neg}$) and positive ($V_{Pos}$) voltage pulse by integrating charging current measured during and calculating a differential charge transfer (DQ) as a difference between charge transfer during the positive and negative charging pulse.

5. A gas sensor adapted to be a potentiometric oxygen sensor in a combustion exhaust stream without the need for a thermocouple mounted in direct proximity of said gas sensor's position and conditioned with an improved pulse discharge technique as described in claim 3.

6. The improved pulse discharge technique of claim 2, further comprising the step:
 (k) calculating analyzed gas concentrations by using said established calibration curves for low, intermediate and high gas concentrations.

7. The improved pulse discharge technique of claim 6, further comprising the step:
 (m) using sensor response values $V_{Neg}$ or $V^{-RT}$ in combination with a differential charge transfer DQ and an iterative data processing algorithm for combined measurements of analyzed gas.

8. A gas sensor adapted to be a potentiometric oxygen sensor in a combustion exhaust stream without the need for a thermocouple mounted in direct proximity of said gas sensor's position and conditioned with an improved pulse discharge technique as described in claim 6.

9. A gas sensor adapted to be a potentiometric oxygen sensor in a combustion exhaust stream without the need for a thermocouple mounted in direct proximity of said gas sensor's position and conditioned with an improved pulse discharge technique as described in claim 7.

10. The improved pulse discharge technique of claim 2, further comprising the step:
 (l) measuring charge transfer during the negative ($V_{Neg}$) and positive ($V_{Pos}$) voltage pulse by integrating charging current measured during charging phases of and calculating a differential charge transfer (DQ) as a difference between charge transfer during the positive and negative charging pulse.

11. A gas sensor adapted to be a potentiometric oxygen sensor in a combustion exhaust stream without the need for a thermocouple mounted in direct proximity of said gas sensor's position and conditioned with an improved pulse discharge technique as described in claim 2.

12. The improved pulse discharge technique of claim 1, further comprising the step:
 (j) establishing calibration curves as a relation between measured ($V^{-RT}$) and analyzed gas concentration ($G_c$) in the form:

$$V^{-RT} \propto \mathrm{Log}\,(G_c)$$

for high analyzed gas concentrations, which are gas concentrations greater than 100 ppm.

13. The improved pulse discharge technique of claim 12, further comprising the step:
 (k) calculating analyzed gas concentrations by using said established calibration curves for different gas concentrations.

14. The improved pulse discharge technique of claim 12, further comprising the step:
 (l) measuring charge transfer during the negative ($V_{Neg}$) and positive ($V_{Pos}$) voltage pulse by integrating charging current measured during charging phases and calculating a differential charge transfer (DQ) as a difference between charge transfer during the positive and negative charging pulse.

15. A gas sensor adapted to be a potentiometric oxygen sensor in a combustion exhaust stream without the need for a thermocouple mounted in direct proximity of said gas sensor's position and conditioned with an improved pulse discharge technique as described in claim 12.

16. A gas sensor adapted to be a potentiometric oxygen sensor in a combustion exhaust stream without the need for a thermocouple mounted in direct proximity of said gas sensor's position and conditioned with an improved pulse discharge technique as described in claim 1.

17. A gas sensor adapted to be a potentiometric oxygen sensor in a combustion exhaust stream without the need for a thermocouple mounted in direct proximity of said gas sensor's position and conditioned with an improved pulse discharge technique as described in claim 1.

* * * * *